United States Patent [19]

Li

[11] Patent Number: 5,879,899
[45] Date of Patent: Mar. 9, 1999

[54] METHODS OF ASSAYING DNA-REPAIRING ENZYMES AND THEIR ALKYLATED DERIVATIVES

[75] Inventor: Benjamin F. Li, Singapore, Singapore

[73] Assignee: National University of Singapore, Crescent, Singapore

[21] Appl. No.: 676,122

[22] PCT Filed: Jan. 13, 1995

[86] PCT No.: PCT/GB95/00064

§ 371 Date: Sep. 16, 1996

§ 102(e) Date: Sep. 16, 1996

[87] PCT Pub. No.: WO95/19445

PCT Pub. Date: Jul. 20, 1995

[30] Foreign Application Priority Data

Jan. 14, 1994 [GB] United Kingdom .................. 9400692

[51] Int. Cl.$^6$ .......................... G01N 33/577; C12N 9/10; C07K 16/40
[52] U.S. Cl. .................. 435/7.24; 435/193; 435/975; 436/518; 436/530; 530/388.26
[58] Field of Search ..................... 435/975, 193, 435/7.24; 530/387.1, 388.1, 388.26; 436/518, 530

[56] References Cited

FOREIGN PATENT DOCUMENTS

WO A 9324837  12/1993  WIPO .

OTHER PUBLICATIONS

Silber, J. R. et al. Cancer Research 53 (14): 3416–3420 Jul. 1993.
Strauss, B. S. Mutation Res. 233: 139–150 Nov. 1990.
Pegg, A. E. et al. Carcinogenesis 12 (9): 1679–1683 1991.
Sedgwick, B. et al. J. Biol. Chem. 263 (9): 4430–4433 Mar. 1988.
Ostrowski, L. et al. Cancer Res. 51: 3339–3344 Jul. 1991.
Wood, W. et al. Biochemistry, A Problems Approach, The Benjamin/Cummings Publishing Co., Menlo Park, CA, pp. 32–36. 1981.
Harlow, E. et al. Antibodies: A Laboratory Manual, Cold Spring Harbor Laboratory, Cold Spring Harbor, NY, pp. 72–77, 92–97, 128–135, 141–157. 1988.
Major, G. N. et al. Biochem. J. 277: 89–96 Jul. 1991.
Pegg, A. E. Cancer Res. 50:6119–6129 Oct. 1990.
Nakatsuru, Y. et al. Proc. Natl. Acad. Sci. USA 90 (14): 6468–6472 Jul. 1993.
MUTAT. RES.(1987), 183(2), 123–7 CODEN:MUREAV; ISSN: 0027–5107, 1987 Teo, I.A. 'Proteolytic processing of the Ada protein that repairs DNA 06–methylquanine residues in *E. coli*'.
Journal of Biological Chemistry, vol. 263, No. 35, 15 Dec. 1988, Baltimore, MD US pp. 19174–19180 Tomori Yoshikai et al. 'Proteolytic Cleavage of Ada Protein That Carries Methyltransferase and Transcriptional Regulator Activities'.
EMBO J. (1984), 3(9), 2151–7 CODEN: EMJODG; ISSN: 0261–4189, 1984 Teo, I. et al. 'Induction of resistance to alkylating agents in *E. coli*; the ada+ gene product serves both as a regulatory protein and as an enzyme for repair of mutagenic damage'.
Cancer Res. (1994), 54(14), 3726–31 CODEN: CNREA8; ISSN: 0008–5472, 15 Jul. 1994 Ayi, Teck–Choon et al. 'A method for simultaneous identification of human active and active–site alkylated 06–methylguanine–DNA thyltransferase and its possible application for monitoring human exposure to alkylating carcinogens'.
Cancer Res. (1992), 52(21), 6052–8 CODEN: CNREA8; ISSN: 0008–5472, 1992 Gonzaga, Prescilla E. et al, 'Identification of the cross–link between human 06–methylguanine–DNA methyltransferase and chloroethylnitrosourea–treated DNA'.
Mutation Research, vol. 145, No. 1/2, Mar. 1985, Amsterdam, NL pp. 1–16 Daniel B. Yarosh 'The role of 06–methylguanine–DNA methyltransferase in cell survival, mutagenesis and carcinogenesis'.
Annual Reviews of Biochemistry, vol. 157, 1988, Palo Alto, CA, US pp. 133–157 Thomas Lindahl et al, 'Regulation and Expression of the Adaptive Response to Alkylating Agents'.

*Primary Examiner*—Frank C. Eisenschenk
*Assistant Examiner*—Evelyn Rabin
*Attorney, Agent, or Firm*—Nixon & Vanderhye P.C.

[57] ABSTRACT

The present invention provides methods of assaying the human DNA repair enzyme $O^6$-methylguanine-DNA methyltransferase (MGMT) and/or active site alkylated derivatives thereof (R-MGMT), which rely on the ability of a protease, e.g., V8 Protease (also referred to as Glu-C Protease), to distinguish between these two enzyme forms. Such a method comprises the steps of: (a) contacting the sample with a protease to which one of human MGMT and R-MGMT is preferentially sensitive; and (b) determining whether the treated sample contains one or more polypeptides selected from (I) at least one polypeptide fragment characteristic of action of the protease on the protease-sensitive form of human MGMT and (ii) the protease-resistant form of human MGMT.

16 Claims, 5 Drawing Sheets

1. Polyclonal

2. Monoclonal (2G1)

Fig.6.

METHODS OF ASSAYING DNA-REPAIRING ENZYMES AND THEIR ALKYLATED DERIVATIVES

The present invention relates to methods of assaying human $O^6$-methylguanine-DNA methyltransferase (MGMT) and/or active site alkylated derivatives (R-MGMT) thereof.

Human MGMT is an important DNA repair enzyme which can transfer alkyl groups from $O^6$-alkylguanine and $O^4$-alkylthymine residues in DNA to a cysteine residue (Cys 167) at the active site of the enzyme. Such alkylated nucleotide residues, which can give rise to transition mutations in DNA sequences by virtue of their miscoding behaviour, can be produced by carcinogenic alkylating agents such as N-nitroso compounds, e.g. N-methylnitrosourea (NMU) and N-ethylnitrosourea (NEU) and N,N-dialkylnitrosamines.

Various human genes associated with tumour formation have been found to carry point mutations, for example ras, p53 and ERCC-3. These mutations are widely believed to be crucial in the activation (oncogenes) or suppression (tumour suppressor genes) of these genes and much evidence supports point mutations arising through the action of alkylating agents on DNA being involved in the etiology of certain human cancers. Thus, it has been shown that a single dose of NMU produces mammary tumours in rats as a result of a G.C to A.T transition mutation in codon 12 of the rat H-ras oncogene. This point mutation can also be generated in vivo by substituting $O^6$-methylguanine for guanine in DNA. As $O^6$-methylguanine is one of the alkylated nucleotides formed by action of alkylating carcinogens on DNA and it can produce the G.C to A.T transition mutation, it is thought to be involved in the formation of mammary tumours in rats exposed to NMU (Zarbl et al. Nature (1985) 315, 382–385; Mitra et al. Proc. Natl. Acad. Sci. USA (1989) 86, 8650–8654).

N,N-dialkylnitrosamines are environmental alkylating agents and have also been shown to be potent tumour inducers in experimental animals (Magee and Barnes Br. J. Cancer, (1956) 10, 114–122). Hence, these chemicals and other alkylating agents which react by the SNI mechanism are considered likely causative agents of human cancers through their ability to produce mutagenic DNA base adducts in vivo (Bartsch et al eds., Relevance of N-Nitroso Compounds to Human Cancer: Exposures and Mechanisms, IARC Scientific Publication no. 84 (1987): International Agency for Research on Cancer, Lyon, France; O'Neill et al eds., Relevance to Human Cancer of N-Nitroso Compounds, Tobacco and Mycotoxins. ibid. no.105 (1991); P. D. Lawley, in Chemical Carcinogens Chapter 7, vol I, Ed. C. E. Searle, ACS Monograph 182, American Chemical Society, Washington, (1984); Vogelstein and Kinzler Nature (1992) 335, 209–210).

Since MGMT can specifically repair these mutagenic lesions in DNA produced by alkylating agents, the level of this enzyme in cells is believed to be a crucial factor in determining the sensitivity of cells towards the tumour-inducing mutagenic action of alkylating carcinogens. (Lindahl et al, Annu. Rev. Biochem. (1988) 57, 133–157; A. E. Pegg, Cancer Res. (1990) 50, 6119–6129). In support of this, it has recently been observed that transgenic mice carrying the human gene for MGMT, targeted for expression in T-cells, exhibit a lower incidence of thymic lymphomas when treated with NMu compared with control non-transgenic mice similarly treated (Dumenco et al. Science (1993) 259, 210–222). Furthermore, MGMT-deficient cell lines have been shown to be highly susceptible to the cytotoxic and mutagenic action of SN1 type alkylating agents (D. B. Yarosh Mutation Research (1985) 145, 1–16; A. E. Pegg, ibid.).

Cellular MGMT also has implications for tumour treatment with chemotherapeutic alkylating agents such as the bifunctional chloroethylating agent 1,3-bis (2-chloroethyl)-1-nitrosourea (BCNU) and other chloroethylnitrosoureas, e.g. 1-(2-chloroethyl)-3-cyclohexyl-1-nitrosourea (CCNU). The chemotherapeutic effect of such drugs depends upon formation of lethal DNA cross-linking base adducts which can be effectively removed by the suicidal repair action of MGMT. Thus, tumour cell lines which are devoid of this enzyme (mer- or mex- tumour cells lines) have been found to be selectively sensitive to treatment with DNA cross-linking alkylating agents such as BNCU. (A. E. Pegg, ibid; Brent et al. Cancer Communications (1989) 5, 323–327).

Convenient means for detecting and distinguishing non active site alkylated human MGMT (hereinafter referred to as human MGMT) and active site alkylated human MGMT (R-MGMT) in biological samples are therefore desired for use, for example, in predicting and monitoring the efficacy of chemotherapy with alkylating drugs in cancer patients. They are also desired for identification of alkylating carcinogens, diagnosis of tumours arising through action of such carcinogens and identification of individuals at high risk of developing such tumours. These individuals may have a lower than normal cellular level of active MGMT and/or a higher than normal cellular level of inactive alkylated MGMT indicative of exposure to one or more alkylating carcinogens.

The inventors for the present invention have now found that alkylation of human MGMT at the active site not only renders the enzyme inactive, but also changes its susceptibility to proteolytic cleavage by the known protease V8. This is a protease of S. Aureus which has been observed under certain circumstances to cleave peptide bonds on the carboxy side of glutamic and aspartic acid residues. It is alternatively referred to as Glu-C Protease. This protease is commercially available from a number of sources, e.g. Boehringer Mannheim and Stratagene.

It has thus been observed by the inventors of the present invention that active site methylated human MGMT (MeMGMT), produced by incubation of recombinant human MGMT with the synthetic oligonucleotide TATAC6mGTATA (where 6mG is $O^6$-methylguanine), is preferentially cleaved by V8 Protease in a distinctive pattern, as compared to non-treated human MGMT or human MGMT treated with the non-methylated synthetic oligonucleotide TATACGTATA. Such cleavage results in the release of an 18 kD polypeptide fragment and/or a 14 kD polypeptide fragment, together with one or two smaller end fragments. It is believed that alkylation of the active site cysteine of human MGMT alters the conformation of the enzyme and as a result certain glutamic acid residues in the protein become more exposed and hence sensitive to recognition by V8 Protease.

N-terminal peptide sequencing of isolated 18 kD and 14 kD fragments arising from V8 Protease action on MeMGMT has shown that their N-terminal sequences are identical and correspond to the isoleucine at codon 31 of human MGMT. Thus, the 18 kD fragment arises from V8 Protease cleavage at the glutamic acid residue at amino acid position 30, while double cleavage at amino acid position 30 and the glutamic acid residue at amino acid position 172 is believed to give rise to the 14 kD fragment.

The discovery that human MGMT and human MeMGMT are sufficiently different in conformation to exhibit differential sensitivity to protease cleavage has enabled the development of assays capable of distinguishing human MGMT and active site alkylated forms of this enzyme and hence suitable for determining the presence of one or both of human MGMT and human R-MGMT in a biological sample, e.g. a human blood sample or an extract of a human tumour biopsy sample. As a particularly preferred embodiment, the present invention provides for the first time a means of simultaneously specifically detecting in a single sample both human MGMT and human R-MGMT.

Thus, according to one aspect of the present invention, there is provided a method of determining the presence of one or both of human MGMT and active site alkylated MGMT (R-MGMT) in a sample, which comprises:

(a) contacting the sample with a protease to which one of human MGMT and R-MGMT is preferentially sensitive; and (b) determining whether the treated sample contains one or more polypeptides selected from (i) at least one polypeptide fragment characteristic of action of the protease on the protease-sensitive form of human MGMT and (ii) the protease-resistant form of human MGMT.

The protease may be any protease which recognises a conformational difference between human MGMT and this enzyme in active site alkylated form so that human MGMT and R-MGMT are differentially sensitive to the protease, only one of these two enzyme forms being substantially cleaved. Preferably, the chosen protease may be V8 Protease or a functional modified form thereof.

In one embodiment, the present invention provides a method of determining the presence of one or both of human MGMT and R-MGMT in a sample, which comprises:

(a) contacting the sample with V8 Protease or a functional modified form thereof; and (b) determining whether the treated sample contains one or more polypeptides selected from (i) at least one polypeptide fragment characteristic of action of V8 Protease on R-MGMT and (ii) intact human MGMT.

In step (b), the treated sample will thus be analysed for the presence of one or more polypeptides selected from (i) intact human MGMT (ii) the 18 kD polypeptide fragment resulting from V8 Protease cleavage of R-MGMT at Glu 30, (iii) the N-terminal 30 amino acid fragment resulting from V8 Protease cleavage of R-MGMT at Glu 30 (iv) the 14 kD polypeptide fragment resulting from V8 Protease double cleavage of R-MGMT and (v) the c-terminal fragment resulting from V8 Protease double cleavage of R-MGMT believed to correspond to amino acid residues 173–207.

The terms "active site alkylated human MGMT" and "R-MGMT" as used herein should be understood to refer broadly to human MGMT carrying at its active site an alkyl group, e.g. a $C_{1-4}$ alkyl group such as a methyl group or an ethyl group, or human MGMT rendered inactive by reaction of the active site cysteine residue with an alternative functionally equivalent inactivating group, e.g. a benzyl group. A sample for a method of the present invention may contain R-MGMT which is heterogenous as regards the active site inactivating group or may contain R-MGMT which is homogeneous as regards this group. For example, the sample may contain R-MGMT which is solely active site methylated MGMT (MeMGMT).

A modified functional form of V8 Protease may be any variant of the native V8 Protease sequence which retains an active site of the same specificity. Such a variant may have one or more amino acid substitutions, deletions or insertions and/or an extension at either or each end so that proteolytic activity is retained. There may be a degree of homology of at least 80%, for example at least 90 to 95%, preferably at least 98% or 99%, between the modified protease and the natural enzyme. Where a modified functional form of V8 Protease incorporates one or more amino acid changes, these will generally be outside of the active site. These may, for example, be conservative substitutions, although other types of substitution may be incorporated which do not destroy protease function. Up to for example 10, for example 1 to 5, amino acid changes, either substitutions, deletions or insertions, may be present which result in retention of proteolytic activity.

Thus, one or more amino acid changes may be present which preserve the physicochemical character of the protease, i.e. its character in terms of charge density, hydrophilicity/-hydrophobicity and configuration, and hence preserve protease function. For example, a hydrophobic amino acid may be replaced by an alternative hydrophobic amino acid, e.g. Trp may be substituted by Phe or vice versa. For example, Ala may be replaced by Val or vice versa, Val by Leu, Lys by Arg, Asp by Glu or vice versa. As mentioned above, this is provided that protease activity is preserved in addition to the physicochemical character of the enzyme.

The detection step (b) of an assay as hereinbefore defined may, for example, be carried out by separating polypeptides of the protease-treated sample on the basis of size. Thus, preferably SDS-polyacrylamide gel electrophoresis (SDS-PAGE) may be carried out and the gel subsequently analysed for the presence of one or more polypeptides of interest, e.g. intact human MGMT and V8 Protease cleavage products of R-MGMT. In this manner, simultaneous detection of human MGMT and R-MGMT may be conveniently achieved.

As a particularly preferred embodiment, the present invention thus provides a method of simultaneously determining the presence of human MGMT and R-MGMT in a sample, which comprises:

(I) contacting the sample with V8 Protease or a functional modified form thereof;

(II) separating the polypeptides of the treated sample by SDS-PAGE; and (III) analysing the gel obtained in step (II) for the presence of (i) at least one polypeptide fragment characteristic of action of V8 Protease on R-MGMT and (ii) intact human MGMT.

Step (III) may be conducted in accordance with any conventional procedure suitable for identification of polypeptides isolated on an SDS polyacrylamide gel. It may, for example, be a conventional silver staining procedure. Preferably, however, steps (II) and (III) will together constitute a conventional Western Analysis protocol. In this case, step (III) will be carried out by the following stages:

(1) transfer of separated polypeptides on the gel to a solid support, e.g. a nitrocellulose support, by a suitable blotting procedure;

(2) contact of the solid support with an anti-MGMT antibody reagent capable of binding SDS-denatured human MGMT and at lease one V8 Protease cleavage product of R-MGMT following SDS-PAGE separation; and (3) detecting any bound anti-MGMT antibody on the solid support.

The term "antibody" as used herein includes complete antibody molecules and antigen binding fragments thereof such as Fab and F(ab')$_2$ fragments. Humanised antibodies and fragments thereof are also included within the term "antibody".

The anti-MGMT antibody reagent employed for Western Analysis in an assay of the present invention for MGMT and R-MGMT may be an anti-human MGMT polyclonal antibody reagent or a monoclonal antibody reagent which recognises both intact human MGMT and a V8 Protease cleavage fragment of R-MGMT following separation by SDS-PAGE. Procedures for obtaining such antibody reagents are described, for example, in Cancer Research (1992) 52, 6423–6430. Preferably, for this purpose a monoclonal antibody reagent will be employed which recognises (i) intact SDS denatured human MGMT and (ii) both the 18 kD and 14 kD polypeptide fragments obtainable by V8 Protease cleavage of human MGMT in active site alkylated form after separation by SDS-PAGE.

Particularly preferred as the anti-MGMT antibody reagent for carrying out such a Western Analysis procedure is the monoclonal antibody of hybridoma cell line ECACC 93112516, which was deposited under the Budapest Treaty at the European Collection of Animal Cell Cultures, Porton Down, UK on the 25th Nov. 1993, or a functional equivalent thereof which competes for binding to the same antigenic determinant. The monoclonal antibody of hybridoma cell line ECACC 93112516, which has been designated monoclonal antibody 2G1, binds an antigenic determinant in the region of SDS denatured MGMT between amino acids 30 and 60 and exhibits high affinity in a Western Analysis procedure for binding of intact MGMT and both the 18 kD and 14 kD fragments characteristic of V8 Protease cleavage of R-MGMT.

When carrying out Western Analysis for assay of human MGMT and R-MGMT in accordance with the present invention, the anti-MGMT antibody reagent employed may be directly labelled with a label giving a detectable signal. Preferably however, binding of the anti-MGMT antibody reagent to the solid support will be determined using a secondary labelled reagent. Thus, for example, the anti-MGMT antibody reagent may be a biotinylated antibody reagent in which case the secondary labelled reagent will be avidin or streptavidin conjugated to a signal-producing label. Most preferably, secondary-labelled antibodies may be employed. Any detectable label conventionally employed for immunoassays may be used, e.g. an enzyme such as horseradish peroxidase, a fluorescent label such as fluorescein or rhodamine or a radiochemical label such as $^{125}$I. Good sensitivity may, for example, be achieved by using a secondary antibody reagent labelled with horseradish peroxidase (HRPO) and detecting binding of this antibody reagent to the solid support using the known enhanced chemiluminescence (ECL) technique.

The sample for an assay of the present invention may be a liquid sample such as a cell extract, e.g. an extract of a leucocyte fraction derived from human blood or an extract of a tumour biopsy sample. The sample may be derived by fractionation of a sample, e.g. a cell extract, using an antibody reagent immobilised on a solid support. Thus, for example, the sample may be a sample enriched for native active human MGMT and active site alkylated human MGMT obtained by subjecting an initial sample to a fractionation step employing a solid support-immobilised antibody reagent capable of binding both these enzyme forms. The antibody reagent for this purpose may, for example, be an anti-MGMT polyclonal antibody reagent or monoclonal antibody 2G1 immobilised on a solid support. The solid support may be used directly as the sample in a method of the present invention following contact with and separation from the initial sample.

The conditions for protease digestion will be non-protein denaturing conditions such that human MGMT and R-MGMT are differentially sensitive to proteolytic cleavage. The optimum conditions for protease digestion will depend upon the sample type and the protease employed. In the case of use of V8 Protease, generally a pH of about 8.0 will be chosen. For a cellular extract, a V8 Protease: cellular protein ratio of about 50 μg: 200 μg may, for example, be employed with an incubation time of about 30 minutes or longer, e.g. 40 minutes, at 37° C. Under these conditions, any R-MGMT is substantially cleaved, while any human MGMT remains substantially intact. It will, however, be apparent to those skilled in the art of biological assays that other conditions may be employed with similar result and may be ascertained by appropriate control experiments.

By virtue of the fact that they enable convenient detection of both human MGMT and active site alkylated human MGMT in biological samples, assay methods of the present invention have many applications relating to tumour diagnosis, prognosis and treatment. Such methods enabling for the first time specific direct identification of active site alkylated human MGMT may be particularly useful in monitoring resistance to chemotherapy with alkylating drugs and in identifying (i) individuals at risk of tumours through exposure to an alkylating carcinogen or (ii) cancer patients having a tumour, where exposure to an alkylating carcinogen is a likely causative agent. Importantly, it has been established by the inventors for the present invention that exposure of individuals to alkylating carcinogens or resistance to alkylating drugs in cancer patients can be particularly conveniently assessed by analysis of blood samples for active site alkylated human MGMT.

Thus, according to an aspect of the present invention, there is provided a method of detecting exposure of a human to an alkylating carcinogen, which comprises determining the presence of active site alkylated MGMT in a sample derived from solid tissue or blood of an individual by means of an assay method as hereinbefore described.

According to yet another aspect of the present invention, there is provided a method of assessing in a cancer patient resistance to chemotherapy with an alkylating drug, which comprises determining the presence of active site alkylated MGMT in a sample derived from a tumour biopsy sample or blood of the patient by means of an assay method as hereinbefore described. Alternatively, or simultaneously, in the case of such a patient, the level of non-alkylated active MGMT may desirably be determined in such a sample by means of an assay method of the present invention. By application of an assay method of the present invention to such samples the ratio of active MGMT to inactive active site alkylated MGMT may desirably be calculated.

Detection of the level of active MGMT in samples using an assay method of the present invention may also find application in identifying individuals with a lower than normal level of this enzyme and hence an increased cancer risk.

According to yet another aspect of the present invention, there is thus provided a method of identifying individuals with an increased cancer risk, which comprises applying an assay method as hereinbefore described to samples derived from human solid tissue or blood and identifying such samples with a lower than normal level of MGMT and/or a higher than normal level of R-MGMT.

For such clinical applications, an assay method as hereinbefore described will most desirably be applied to a treated blood sample, preferably a leucocyte fraction extract. A blood sample of not more than a few mls such as 1–20 mls, e.g. about 5–10 mls, will generally suffice for application of a method of the present invention.

An assay method of the present invention may additionally advantageously be employed to enable convenient screening of drugs for use as alkylating chemotherapeutic agents and to identify alkylating carcinogens. Such an assay method may further be employed to assess the potency of a DNA alkylating chemotherapeutic or carcinogenic agent.

In a further aspect, the present invention thus provides a method of identifying an alkylating chemotherapeutic or carcinogenic agent in a sample which comprises:

(i) contacting human cells in vitro, e.g. cultured human cells or human blood, with the said sample, (ii) preparing a cellular extract of cells thus treated, and (iii) assaying R-MGMT in the cellular extract using an assay method as hereinbefore described.

The cellular extract assayed may, for example, conveniently be an extract of a leucocyte fraction derived from human blood (see Example 3). Suitable cell cultures for such an assay include, for example, a culture of CEM cells (see Example 2B).

In yet another aspect, the present invention provides a method of assessing the potency of an alkylating chemotherapeutic or carcinogenic agent which comprises:

(i) contacting populations of human cells in vitro with different concentrations of the said agent, (ii) preparing a cellular extract of cells from each population following treatment as in step (i), and (iii) assaying R-MGMT in each cellular extract using an assay method as hereinbefore described.

The reagents needed to perform an assay method according to the present invention may be conveniently packaged into a kit. Thus, in a still further aspect the invention provides a kit comprising a protease to which one of the human MGMT and R-MGMT is preferentially sensitive, e.g. V8 Protease or a functional modified form thereof, and one or more antibody reagents for performing an assay method as hereinbefore described, containerised for storage and transport. Such a kit may comprise, for example (a) monoclonal antibody 2G1 or a functionally equivalent Ig reagent and V8 Protease or (b) V8 Protease, an anti-MGMT antibody reagent immobilised on a solid support, e.g. the walls of a microtitre plate, and monoclonal antibody 2G1 or a functionally equivalent Ig reagent. A kit as in (a) or (b) above may further include an appropriate labelled anti-IgG antibody reagent, preferably, for example, an anti-IgG antibody reagent labelled with horseradish peroxidase. A kit according to the present invention for clinical application of an assay method as hereinbefore described may also for convenience include a vessel for collection of an appropriate blood sample.

In the following Examples, the present invention is illustrated with reference to the following Figures.

Each sample contained 200 μg of total cellular protein. Panel A: no V8 Protease treatment. Panel b: Samples treated with V8 Protease. C=control, DMSO=control from CEM cells treated with vehicle dimethylsulphoxide at 0.15%, NMU=treated with N-methylnitrosourea, NEU=treated with N-ethylnitrosourea and BCNU=treated with 1,3-bis(2-chloroethyl)-1-nitrosourea. Western analysis was carried out using polyclonal anti-MGMT antibodies with an ECL time of 2 mins.

Each sample contained 200 μg of total cellular protein. Panel a: no V8 Protease treatment. Panel b: Samples treated with V8 Protease. C=control; DMSO=control from CEM cells treated with vehicle dimethylsulphoxide at 0.2%; 0.1, 0.25, 0.5, 1.0, 1.5 and 2.0 mM represent concentrations of N-methylnitrosourea (NMU) used. Western Analysis was carried out using anti-MGMT polyclonal antibodies and monoclonal antibody 2G1 with ECL times of 2 and 6 mins respectively.

Each sample contained 200 μg of total cellular protein. Panel a: no V8 Protease treatment. Panel b: Samples treated with V8 Protease. DMSO=control from CEM cells treated with vehicle dimethylsulphoxide at 0.15%. Recovery times investigated were 0 (immediately after drug treatment), 1, 2 and 3 hrs. Western Analysis was carried out using polyclonal anti-MGMT antibodies and monoclonal antibody 2G1 with ECL times of 2 and 6 mins respectively.

Each lane contained 200 μg of protein from a leucocyte extract.

| Panel A: | N1–N9 = blood samples obtained from normal males age 25 to 45 one hour after breakfast. P1, P2 = blood samples obtained from post-chemotherapy individuals (see Table 1 for treatment histories). |
|---|---|
| Panel A.1 | = direct Western Analysis without V8 Protease treatment. |
| Panel A.2 | = Western Analysis after V8 Protease treatment. |
| I | = intensity determined by densitometer (Ultroscan SL, LKB, Sweden). |

Panels B1 and B2: blood samples taken from patients undergoing chemotherapy (Western Analysis after V8 Protease treatment).

Panel B1=patients treated with cyclophosphamide.

Panel B2=patients treated with CCNU.

See Table 1 for patient and drug administration details. Times shown indicate time after drug administration each blood sample was taken.

Panel B3: fresh human blood samples treated with NMU. DMSO=control treated with 0.15% vehicle dimethylsulphoxide. 0.21, 0.75 and 1.5 mM=concentrations of NMU used.

Western Analysis was carried out using monoclonal antibody 2G1. The ECL time for Panels A.1 and B1 was 6 minutes. The ECL time for Panels A2, B2 and B3 was 8 minutes.

EXAMPLES

Methods:

a. Protein measurements: by Lowry (Sigma, USA) with TCA precipitation.

b. Cell culture: CEM cells (ATCC, USA) were grown in 50% MEM/RPM1 and Hela S3 cells (ATCC, USA) were grown in MEM with 10% FBS and supplements. Cells at the log phase were harvested by spinning at 500 g, washed once with Hanks' BSS buffer and stored as a pellet at −80° C.

c. Preparation of cell extracts: Cell extracts were prepared by sonification (3 pulses of 10 s each) after resuspension of the cells in 2×PCV (pack cell volume) of buffer A (0.3 M NaCl, 1 mM EDTA, 50 mM Tris.Cl pH 8, 3 mM DTT and 3% glycerol). The inclusion of 0.3M Nacl in the extraction buffer is important for the quantitative recovery (>90%) of MGMT from cells exposed to N-alkylnitrosoureas. Phenylmethanesulphonyl fluoride (PMSF) was added immediately (final concentration 10 μg/ml). The samples were then spun at 50,000 g for 30 mins at 4° C. Aliquots of the supernatants were stored at −80° C.

d. Drug treatment of cell cultures: All drugs used were diluted from IM stock solutions in dimethylsulphoxide (DMSO). 100 ml samples of cell culture (per single condition) were pelleted, washed and resuspended in 20 ml of serum free medium (pH 7.5) before the addition of drugs or vehicle DMSO. Drug treatments were of 30 mins duration under this serum free condition. For recovery experiments after drug treatment, samples were diluted with complete medium (with FES) to original volume. In the case of drug-treated samples for analysis without recovery, cells were immediately pelleted and washed with 20×PCV of Hanks' BSS and stored as a pellet at −80° C.

e. V8 Protease digestion: 200 μg of total cellular protein was treated with 50 ηg of V8 Protease (Boehringer Mannheim, Germany) in a final volume of 15 μl of buffer A (0.3M NaCl, 1 mM EDTA, 50 mM Tris.Cl pH8, 3 mM DTT and 3% glycerol) for 40 mins at 37° C.

V8 Protease digestion of R-MGMT in CEM and Hela S3 extracts is completed in the first 30 minutes under these conditions. For human total leucocyte extracts (since they were obtained from different individuals) 40 and 70 minutes incubation times were investigated simultaneously. No difference in the cleavage patterns was observed with the longer incubation time. The data obtained with 40 minutes incubation is given herein. This is the standard protocol for V8 Protease digestion unless otherwise stated.

After incubation, 5 μl of 4×Laemmli loading buffer was added and the sample was boiled at 95° C. for 10 mins.

f. Western Analysis: Samples (200 μg of V8 Protease treated or untreated cellular protein/lane) were resolved by 15% SDS-PAGE (in the presence of 1 mM EDTA) and transferred to a nitrocellulose membrane by electroblotting before visualisation by anti-MGMT polyclonal antibodies (3μg/ml) or monoclonal antibody 2G1 (6 μg/ml) as described in Cancer Res. (1992) 52 6423–6430. The filters were blocked overnight at 4° C. with a saturated solution of ovalbumin in TBS buffer [20 mM Tris.HCl(pH 8): 0.9% NaCl solution]. The filters were then incubated with antibodies in TBS-TW20, i.e. TBS buffer with 0.05% Tween 20 (1 hr with polyclonal antibodies and 2 hrs with the monoclonal antibody) at 37° C. After three 5 minute washes with TBS-TW20, the membranes were incubated with secondary antibodies (Hyclone, USA): anti-rabbit HRPO-anti-IgGs for the polyclonal anti-MGMT antibody reagent (30 mins) and anti-mouse HRPO-anti IgGs (120 mins) for the monoclonal antibody reagent at 37° C. The filters were then washed as above before being visualised by ECL (Enhanced Chemiluminescence) using an ECL reagents kit as supplied by Amersham (U.K.).

g. Recombinant human MGMT: This protein was prepared as described in Cancer Research (1992) 52 6423–6430.

h. Active-site methylated human MGMT (MeMGMT): This protein was also prepared as described in Cancer Research (1992) 52, 6423–6430 by using the synthetic oligonucleotide TATAC6mGTATA to treat recombinant human MGMT.

i. Rabbit polyclonal anti-MGMT antibodies: Anti MGMT Polyclonal antibodies were obtained as described in Cancer Res. (1992) 52 6423–6430. Rabbits were given injections of recombinant human MGMT (100 μg/animal, fraction 8 of the final single-stranded DNA column) every 4 weeks. High-affinity polyclonal antibodies (identified by Western blotting analysis of the serum) were obtained from the seventh boost. The serum was then further purified with a recombinant MGMT affinity column (1 mg coupled to 200 μl packed gel volume, CNBr-activated Sepharose). The antibody-antigen matrix was washed with 1M NaCl before eluting with glycine.

(Harlow, E. and Lane, D. Antibodies. A Laboratory Manual. Cold Spring Harbor, N.Y.: Cold Spring Harbor Laboratory, 1988)

j. Mouse monoclonal antibody capable of binding human MGMT and the 18 kD and 14 kD cleavage fragments obtained by V8 Protease digestion of MeMGMT. The protocols for immunisation and fusion were followed exactly as described by Harlow and Lane (Antibodies. A Laboratory Manual. Cold Spring Harbor, N.Y.: Cold Spring Harbor Laboratory, 1988). BALB/c mice were given injections of an immunising preparation of MeMGMT obtained as follows: 100 μl containing 120 μg of MGMT from fraction 8 of a single-stranded DNA preparation column was added to a solution (30 μl) containing 4 absorbency at 260nm of TATAC6mGTATA in buffer consisting of 50 mM Tris.HCl pH 8.0, 1 mM EDTA and 5 mM DTT; the solution was then incubated at 37° C. for 30 mins before mixing with Freund's adjuvant (1:1) for injection into 4 mice. Spleen cells from immunized mice (after 9 months) were fused with AG8 cells (ATCC, USA). The fusion cells were plated out in 18-x 96-well tissue culture plates. The clones were screened by ELIZA using 96-well immunoplates coated with either recombinant human MGMT or MeMGMT. Positive clones were further screened by Western blotting. From these clones, one clone (2G1) was identified producing an antibody also exhibiting binding in the presence of the 18 kD and 14 kD polypeptide fragments obtained by V8 Protease cleavage of MeMGMT.

k. Preparation of total leucocyte extract from human blood. 5–10 ml of EDTA treated blood was spun in a leucoprep tube (Becton Dickinson, USA) at 1700 g for 30 minutes at 20° C. The interphase leucocyte layer was then removed and washed twice with 15 ml PBS (recovered by spinning at 350 g for 10 minutes). The cell pellets were then frozen and cell extracts were prepared as described in method c. above.

EXAMPLE 1 a(i) Use of V8 Protease and SDS-PAGE to distinguish Human MGMT and Human MeMGMT

It has previously been shown that treatment of recombinant human MGMT with the synthetic oligonucleotide TATAC6mGTATA, prepared as described by Li and Swann in Biochemistry (1989) 28, 5779–5786, generates inactive methylated MGMT (Ayi et al. Cancer Res. (1992) 52, 6423–6430, Liem et al. J. Mol. Biol. (1993) 231, 950–959)

Samples containing 1 g (by Bradford) of recombinant human MGMT were treated as follows:
(i) control MGMT with no treatment;
(ii) treated with V8 Protease as in method e. above;
(iii) treated with 0.01 OD (at 260 nm) of TATACGTATA at 37° C. for 10 mins before V8 Protease addition;
(iv) treated with 0.01 OD (at 260nm) of TATAC6mGTATA before V8 Protease addition; and
(v) treated with 0.1 OD (at 260nm) of TATACGTATA before V8 Protease addition.

Figure 1:
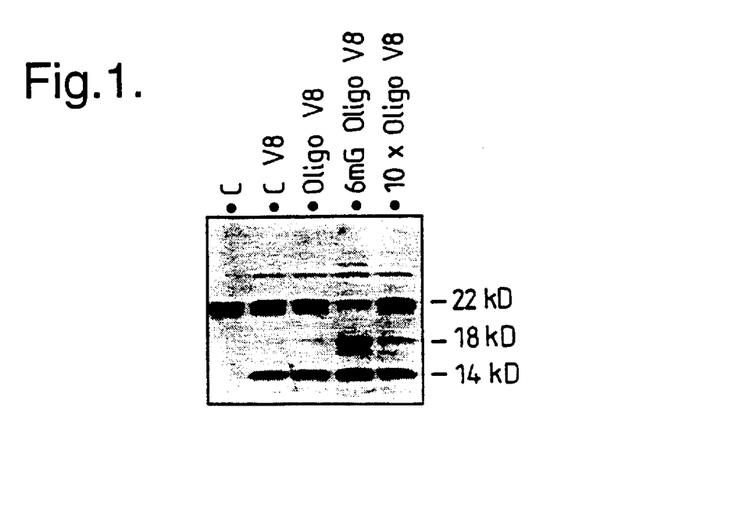
FIG. 1: Identification of active site methylated human MGMT, derived from recombinant human MGMT by oligonucleotide treatment, using V8 Protease and SDS-PAGE 1 μg of MGMT was used for each sample and treated with V8 Protease. C=control MGMT with no V8 treatment, C V8=MGMT treated with V8, Oligo V8 MGMT pretreated with 0.01 OD (at 260nm) of TATACGTATA at 37° C. for 10 mins before V8 digestion, 6 mG Oligo V8=MGMT pretreated with 0.01 OD of TATAC6mGTATA (where 6mG= $O^6$-methylguanine) and 10x Oligo V8=MGMT pretreated with 0.1 OD of TATACGTATA. Polypeptides in the samples were resolved by 15% SDS-PAGE and visualized by silver staining.

Polypeptides in the samples were resolved by 15% SDS-PAGE and visualised by silver staining. The results as shown in FIG. 1 indicate that MeMGMT, produced by incubation of recombinant human MGMT with the oligonucleotide TATAC6mGTATA, is preferentially cleaved by V8 Protease to give a distinct polypeptide fingerprint consisting of an 18 kD fragment band and 14 kD fragment band. Low levels of similar fragments which were observed with samples containing recombinant MGMT treated with V8 Protease are believed to originate from some incorrectly folded molecules. This is consistent with the observation that such MGMT is only 60% active and no V8 Protease cleavage being observed with MGMT in a cell extract (see Example 2). It is evident from FIG. 1 that V8 Protease in conjunction with SDS-PAGE can conveniently enable differential identification of active and active site methylated human MGMT in vitro.

a.(ii) Comparative Example Using Trypsin

The protocol set out in (ai) above was repeated using trypsin instead of V8 Protease. Again, MeMGMT (produced by incubation of recombinant MGMT with the synthetic oligonucleotide TATAC6mGTATA) was observed to be preferentially sensitive to protease digestion. However, a less distinct polypeptide fingerprint was obtained. Hence, trypsin, unlike V8 Protease, is not highly suitable for use in distinguishing MGMT and active site alkylated MGMT.

b. Identification of the 18 kD and 14 kD Polypeptide Fragments Obtained by V8 Protease Cleavage of human MeMGMT.

A 20 x scale of sample (iv) above, following treatment with V8 Protease, was concentrated by TCA precipitation and neutralised with IM Tris, pH 6.8 before resolution of the polypeptides by 15% SDS-PAGE. The polypeptides were then transferred to PVDF membrane and N-terminal sequencing was carried out using the Sequence-Net procedure (Millipore, USA) on a Milligene 6600 Sequencer.

The isolated 18 kD and 14 kD polypeptide fragments were found to have an identical N-terminus showing that the 18 kD fragment arises from cleavage at Glu 30, while the 14 kD fragment arises from cleavage at Glu 30 and, possibly, Glu 172.

EXAMPLE 2

Use of V8 Protease and Western Analysis to Distinguish Human MGMT and Active Site Alkylated MGMT In Cell Extracts A. Identification of MeMGMT in cell extracts treated with the synthetic oligonucleotide TATAC6mGTATA CEM and Hela S3 cell extracts were prepared in accordance with methods b. and c. above and samples were treated as follows:
(i) not treated;
(ii) treated with V8 Protease as in method e. above;
(iii) treated with 10×490 pM of TATACATATA for 15 minutes at 37° C. before addition of V8 Protease;
(iv) treated with 490 pM of TATAC6mGTATA before addition of V8 Protease;
(v) treated with 10×490 pM of TATACGTATA before addition of V8 Protease.

Figure 2:
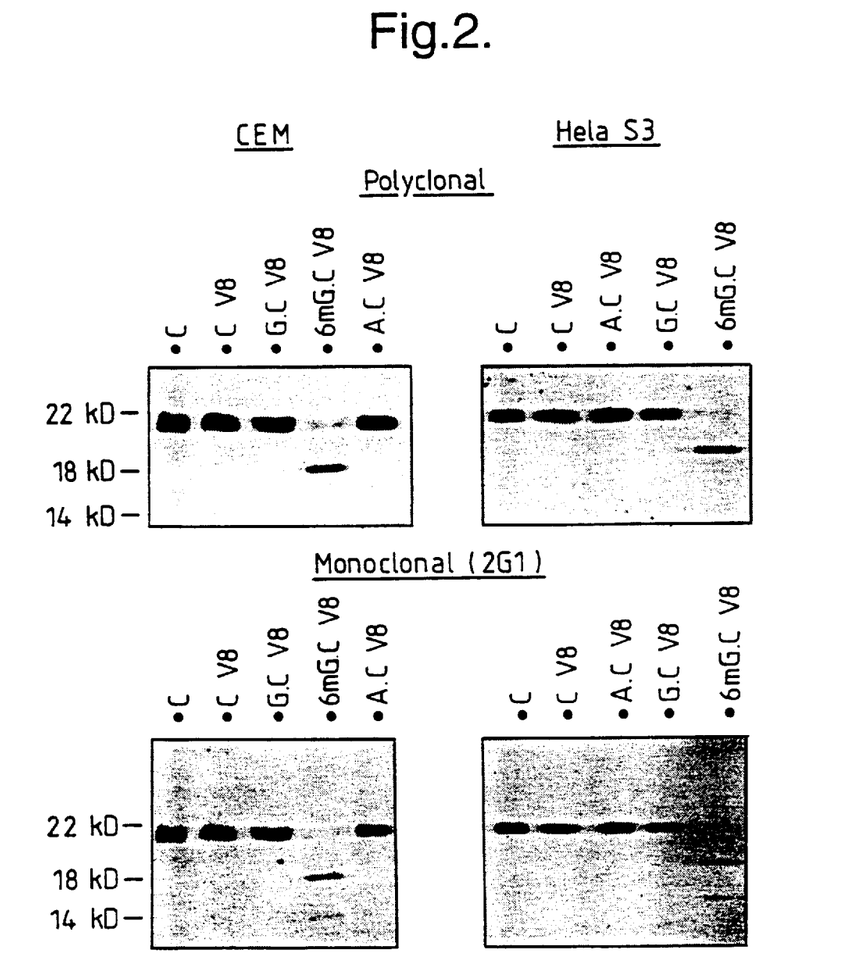
FIG. 2: Identification of active site methylated human MGMT in CEM and HeLa S3 cell extracts treated with various oligonucleotides by Western Analysis of V8 Protease digests Each lane contained 200 μg of total cellular protein which was estimated to contain 190 pM of MGMT. C=untreated cell extract, CV8=cell extract treated with V8 Protease, A.C. V8=cell extract pretreated with 10 ×490 pM of TATA-CATATA for 15 mins at 37° C. before digestion with V8 Protease, 6mG.C V8=cell extract pretreated with 490pM of TATAC6mGTATA before digestion with V8 Protease and G.C V8=cell extract pretreated with 10×490pM of TATACGTATA before digestion with V8 Protease. Western Analysis was carried out using anti-MGMT polyclonal antibodies and monoclonal antibody 2G1 with ECL times of 2 and 6 mins respectively.

Western Analysis was performed with each sample using anti-MGMT polyclonal antibodies and monoclonal antibody 2G1 as shown in FIG. 2.

Both antibody preparations gave similar results in the case of the cell extracts treated with the oligonucleotide TATAC6mGTATA and digested with V8 Protease. A distinct band corresponding to an 18 kD polypeptide was observed with these samples. This band was not observed with any of the other samples.

Thus, significantly MGMT protein in untreated cell extracts was found to be completely resistant to V8 Protease digestion. Furthermore, no cleavage of MGMT was observed when cell extracts were treated with 10 fold excess of TATACATATA oligonucleotide containing an A.C mismatch. This mismatch has a similar helical destabilising effect as TATAC6mGTATA (Wong et al. J. Mol. Biol (1992) 228, 1137–1146). This suggests that V8 Protease recognises R-MGMT and abnormal DNA structure does not induce MGMT to be cleaved by the protease under the conditions employed. The ability of V8 Protease to selectively cleave R-MGMT in cell extracts indicates that active MGMT and R-MGMT exhibit intrinsically different but stable conformations.

B. Identification of Active Site Alkylated MGMT in extracts prepared from cells exposed to various alkylating agents.

Identification of active site alkylated MGMT in extracts prepared from cells treated with various alkylating agents was also investigated by Western Analysis of V8 Protease digests. CEM cells were treated with 1.5 mM of one of the following alkylating agents for 30 mins at 37° C.: N-methylnitrosourea (NMU), N-ethylnitrosourea (NEU) and the chemotherapeutic agent 1,3-bis(2-chloroethyl)-1-nitrosourea (BCNU). Control cell cultures were also treated with dimethylsulphoxide at 0.15%. One set of extract samples prepared as in method c. above was treated with V8

Figure 3:
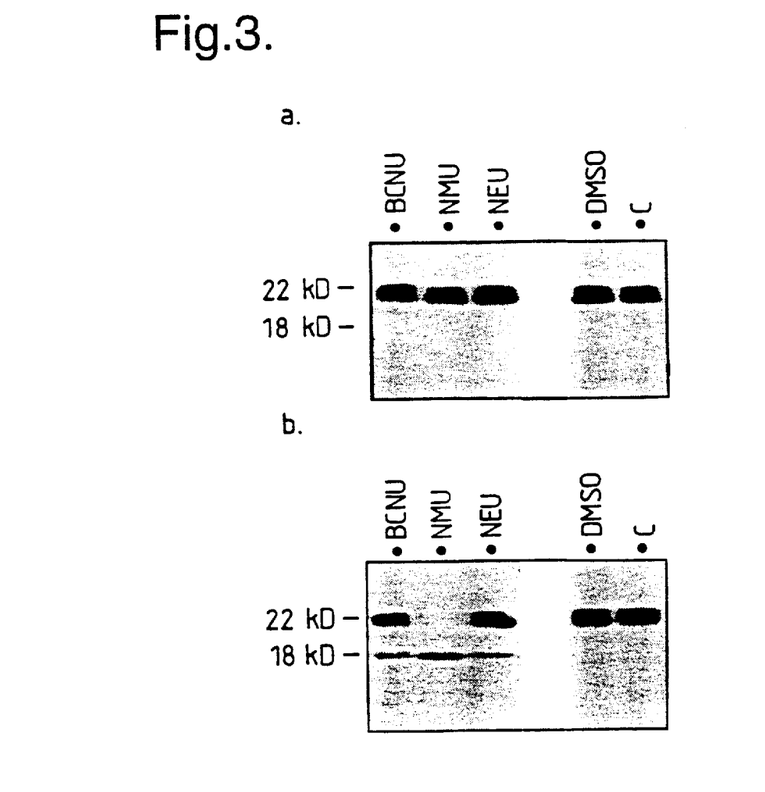
FIG. 3: Identification of active site alkylated human MGMT in cell extracts from CEM cells treated with 1.5 mM of various alkylating agents for 30 mins at 37° C. by Western Analysis of V8 Protease digests.

Protease and a further set of extract samples received no V8 Protease treatment. The samples were analysed by Western Analysis using polyclonal anti-MGMT antibodies and an ECL time of 2 minutes. The results are shown in FIG. 3.

It is apparent that MGMT was completely in the active site methylated form and sensitive to V8 Protease in extracts from cells treated with NMU since all V8 Protease treated extracts of such cells gave an 18 kD band, but not a 22 kD band. In the case of extracts from cells treated with NEU or BCNU prior to V8 Protease addition, an 18 kD polypeptide fragment could be detected, but some uncleaved MGMT remained. The reason for the lesser extent of MGMT protein cleavage observed with the two ethylating agents is not known. Less efficient cleavage of ethylated MGMT than methylated MGMT by V8 Protease has, however, been eliminated since prolonged V8 Protease digestion did not alter the cleavage patterns observed (data not shown).

Figure 4:
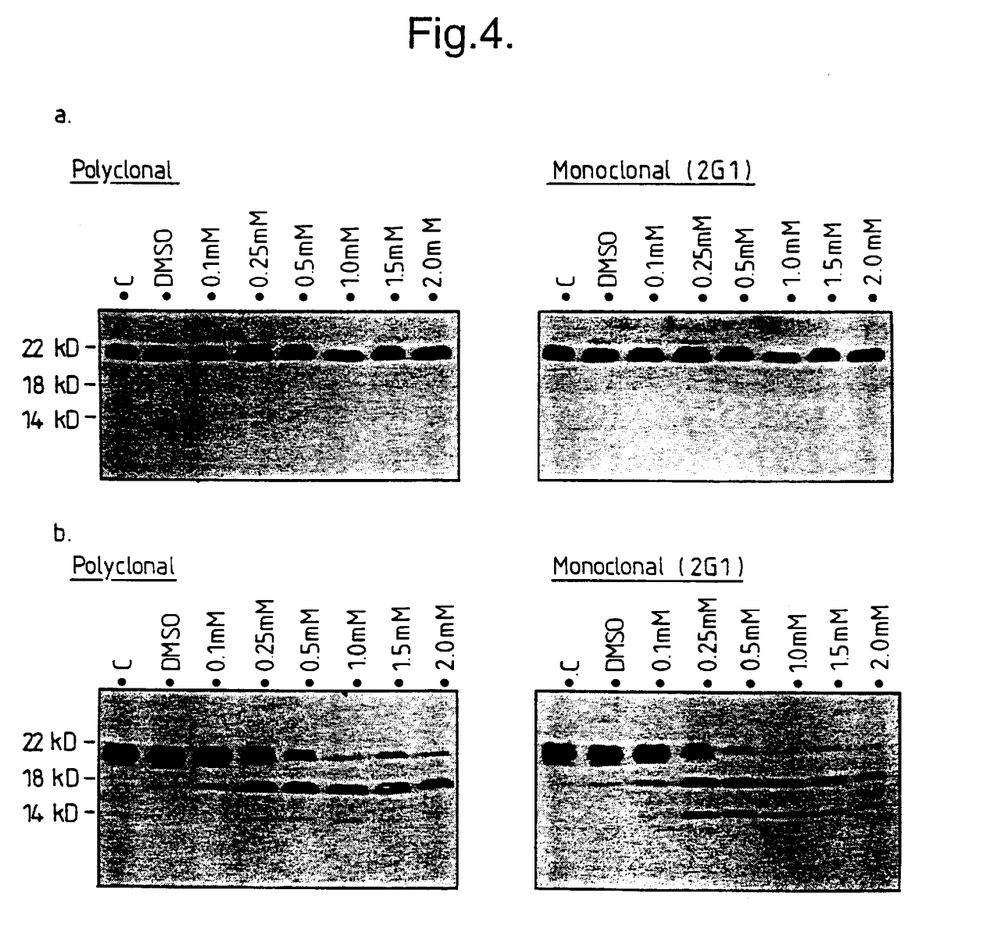
FIG. 4: Dose Response analysis of active site methylated human MGMT in cell extracts of CEM cells treated with various concentrations of NMU for 30 mins at 37° C. using V8 Protease and Western Analysis.

C. Dose response analysis of MeMGMT in extracts from cells treated with various concentrations of an SN1-alkylating agent CEM cells were treated with various concentrations of NMU for 30 minutes at 37° C. in accordance with method d. above. Control cell cultures were also treated with dimethylsulphoxide at 0.2%. Cell extracts were prepared as in method c. above and one set of extracts was subjected to V8 Protease treatment while a further set of extracts received no V8 Protease treatment. The samples were analysed by Western Analysis using polyclonal anti-MGMT antibodies and monoclonal antibody 2G1 with ECL times of 2 and 6 minutes respectively. The results are shown in FIGS. 4a and 4b.

In the case of samples receiving no V8 Protease treatment, only a 22 kD band was observed indicative of the presence of uncleaved MGMT/MeMGMT. In the case of the samples from NMU-treated cells to which V8 Protease was added, an 18 kD polypeptide band was observed with all samples. Using monoclonal antibody 2G1, a 14 kD polypeptide band was additionally observed with samples from cells treated with NMU in the concentration range 0.25 mM–2.0 mM. It is apparent from FIG. 4b, referring either to the polyclonal or monoclonal antibody results, that there is a dose response relationship between the amount of V8 Protease sensitive MGMT protein and exposure of CEM cells to NMU at concentrations between 0.1 and 1 mM. Interestingly, the results indicate that 30 minutes exposure of CEM cells to 1mM NMU results in the complete conversion of active MGMT to R-MGMT.

D. Stability of MeMGMT in cell extracts

CEM cells were treated with 1.5 mM NMU for 30 minutes at 37° C. Samples were either immediately spun down or diluted into FBS-containing medium and spun down after 1, 2 or 3 hrs as described in method d. above. Control cell cultures were treated with DMSO. Cell extracts were prepared as described in method c above. One set of samples containing 200 μg of total cellular protein was treated with V8 . Protease and a second set of samples received no V8 Protease treatment. The samples were subsequently analysed by Western Analysis using polyclonal anti-MGMT antibodies and monoclonal antibody 2G1 and ECL times of 2 and 6 minutes respectively.

Figure 5:
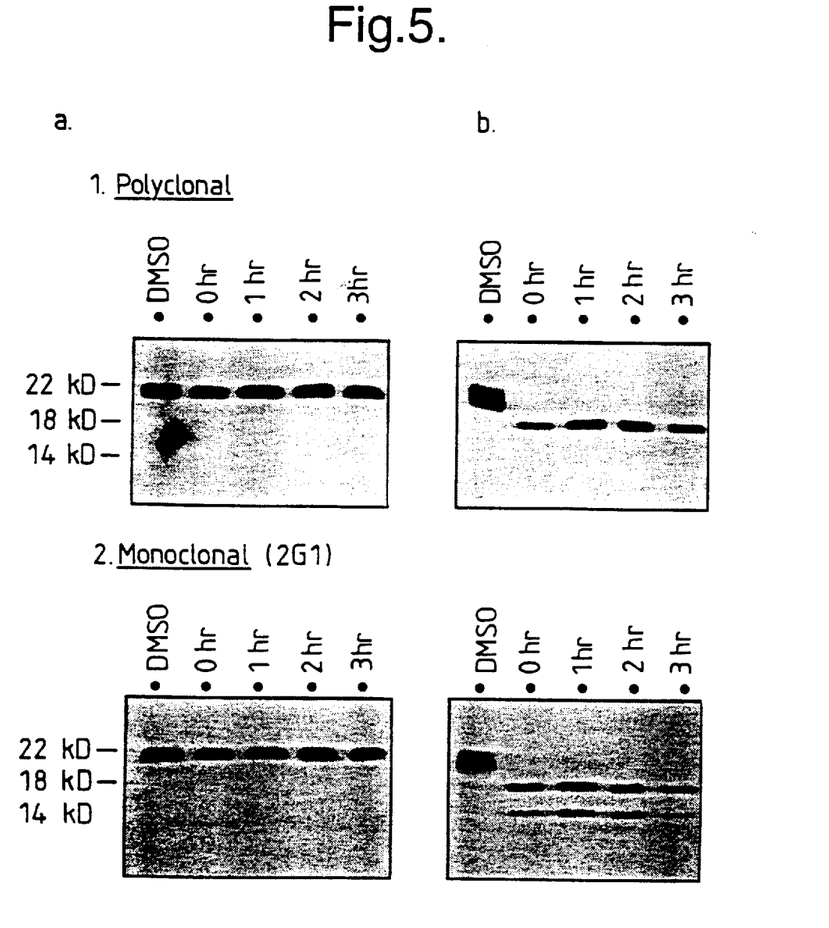
FIG. 5: Determination using V8 Protease and Western Analysis of the stability of active site methylated human MGMT in cell extracts from CEM cells treated with 1.5 mM NMU for 30 mins at 37° C.

The results shown in FIGS. 5a and 5b demonstrate that MeMGMT shows a good degree of stability in CEM cells. No active MGMT was detected during the recovery period studied.

EXAMPLE 3

Identification of MGMT And Active-Site Alkylated MGMT in Extracts of Leucocyte Fractions Obtained From Human Blood 5–10 ml samples of EDTA-treated blood from 10 healthy individuals (males aged 25 to 45) and a number of cancer patients either undergoing chemotherapy or post-chemotherapy (see Table 1) were treated as in method k above to obtain a leucocyte extract.

To simulate human exposure to an alkylating carcinogen, fresh human blood was also treated with NMU. For this experiment, 80 ml of EDTA-treated blood from a single individual was aliquoted to 4×20 ml. Each 20 ml blood sample was treated with either 0.15% of vehicle dimethyl-sulphoxide or NMU (0.21 mM, 0.75 mM or 1.5 mM) at 37° C. for 30 mins before preparation of a leucocyte extract.

Figure 6:
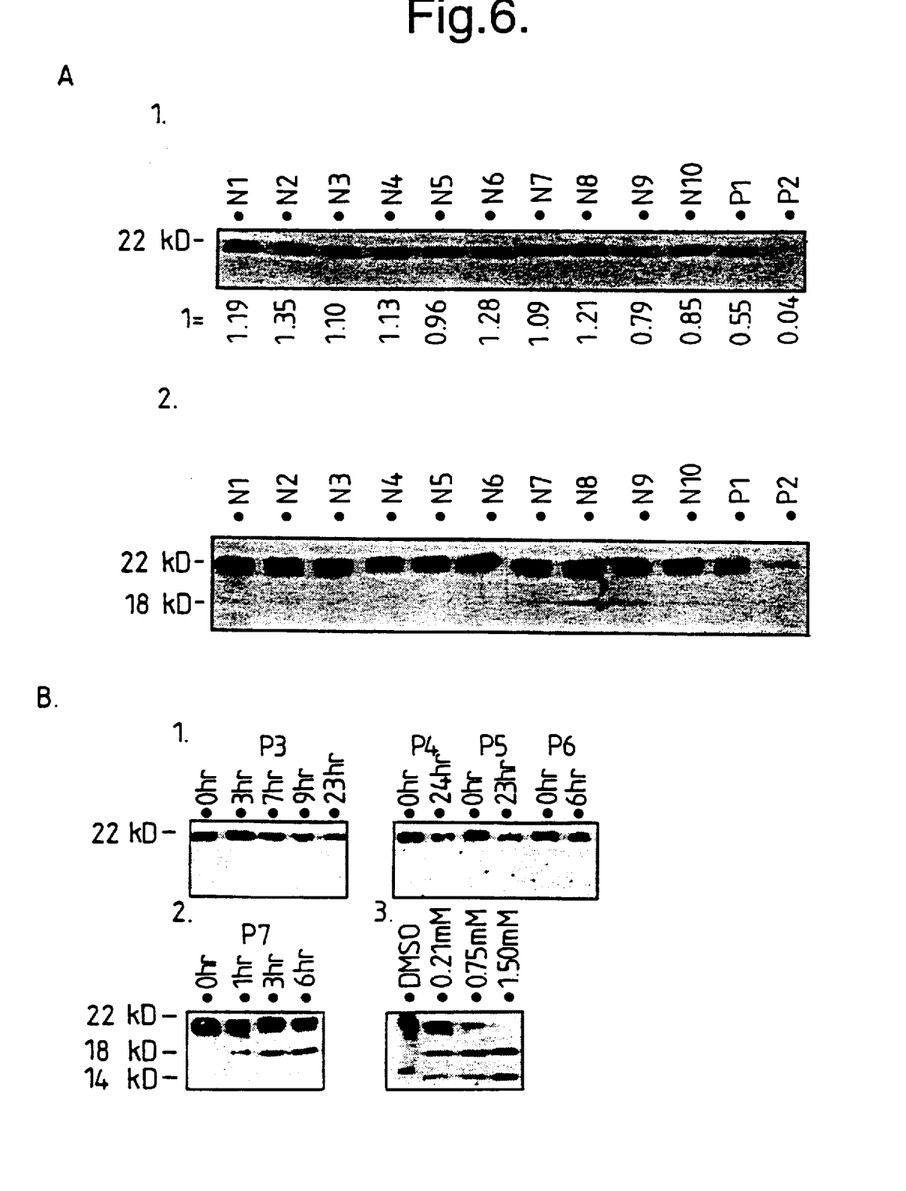
FIG. 6: Identification of MGMT and R-MGMT levels in Extracts of leucocyte fractions obtained from Human Blood Samples using V8 Protease and Western Analysis.

MGMT and R-MGMT were assayed in the leucocyte extract samples using V8 Protease and Western Analysis with monoclonal antibody 2G1 in accordance with method e. above. The results are shown in FIG. 6.

1. Normal individuals

The data obtained with blood samples from the 10 healthy individuals showed that the normal blood leucocyte level of MGMT is 11±4 ng/200 μg of total leucocyte protein (quantified using recombinant MGMT at known concentration). Interestingly, V8 Protease analysis of these samples revealed a small amount of R-MGMT in the blood of one individual (see the 18 kD polypeptide band in Lane N8 of FIG. 6A.2).

2. Cancer Patients

Analysis of the total leucocyte extracts derived from blood samples of patients P1–P7 showed that R-MGMT could be detected in the CCNU-treated patient (see results for patient P7 in FIG. 6B.2) but not in cyclophosphamide treated patients (see results for patients P3–P6 in FIG. 6B.1) No 18 kD polypeptide band could be observed with leucocyte extract samples from patients P3–P6 even after long ECL exposure and twice the standard time for V8 Protease digestion (data not shown).

Interestingly, a progressive decrease in the level of active MGMT (MGMT protein insensitive to V8 Protease) was observed in all cyclophosphamide treated patients. This finding is of particular importance because it correlates with a similar study showing that the activity of MGMT (by assay using radiolabelled $O^6$-methylguanine substrate) decreases in most cyclophosphamide treated patients (Lee et al Br. J. Cancer (1992) 66, 331–336). Patient P2, who had previously been treated by chemotherapy with drugs including cyclophosphamide, was found to have a non-detectable level of leucocyte MGMT (see lane P2 in FIG. 6A). It is thus possible that human cancers that arise from cyclophosphamide chemotherapy are related to drug-induced MGMT-deficiency since MGMT-deficient cells are more prone to mutagenesis by alkylating agents.

The R-MGMT detected in the CCNU treated patient was low (~5%). The ability of the assay studied to detect increasing levels of R-MGMT with time in the CCNU treated patient shows its potential for monitoring $O^6$-alkylguanine formation resulting from exposure to DNA alkylating agents such as CCNU. This is further supported by the results obtained for fresh human blood samples treated with NMU.

3. Blood samples treated with NMU

Similar results were obtained as with CEM cells treated with NMU (see Example 2). Thus, analysis of the leucocyte extracts derived from the NMU treated blood samples (see FIG. 6B.3) showed that the extent of MGMT protein cleaved by V8 Protease was related to the dose of NMU used.

TABLE 1

Patients' records

| Patient | age/sex/wt | disease | pretreatment | during treatment (major) |
|---------|-----------|---------|--------------|--------------------------|
| P1 | 26/F/NA | ALL | Da, Cy | 5 days after pre-treatment |
| P2 | 63/M/NA | MY | Cyclo, Ad, Vi, Pr | 10 days after pre-treatment |
| P3 | 15/F/27 kg | MB(R) | Rad | Cyclo, 0.5 gm, iv |
| P4 | 27/F/60 kg | ALL | Vi, Me | Cyclo, 1.0 gm, iv |
| P5 | 32/F/49 kg | LYM | Rad, Vi, Me | Cyclo 1.0 gm, iv |
| P6 | 40/F/55 kg | BC | Me, Cy, Da, | Cyclo, 1.0 gm, iv |
| P7 | 5/F/18 kg | MB | Rad, Vi | CCNU, 100 mg, oral |

ALL = acute lymphocytic leukemia,
MY = myeloma,
MB(R) = medullablastoma (recurrent),
LYM = lymphoma,
BC = breast carcinoma,
Da = daunorubicin,
Cy = cytarabine,
Cyclo = cyclophosphamide,
Ad = adriamycin,
Vi = vincristine,
Pr = prednisolone,
Me = methotrexate,
Rad = radiotherapy,
CCNU = 1-(2-Chloroethyl)-3-cyclohexyl-1-nitrosourea,
iv = intravenous and
N.A. = not available.

I claim:

1. A method of determining the presence of active site alkylated human MGMT (R-MGMT) in a sample, which comprises:
   (a) contacting the sample with V8 Protease or a functional modified form thereof; and
   (b) determining whether the treated sample resulting from step (a) contains at least one polypeptide fragment characteristic of action of V8 Protease on R-MGMT.

2. A method as claimed in claim 1 wherein said at least one polypeptide fragment of said treated sample is subjected to SDS-polyacrylamide gel electrophoresis.

3. The method as claimed in claim 1 wherein the presence of said at least one polypeptide fragment is determined by a Western Analysis procedure.

4. The method according to claim 3 wherein monoclonal antibody 2G1, obtainable from hybridoma cell line ECACC 93112516, or a functional equivalent thereof, is employed for said Western Analysis.

5. The method according to claim 1 wherein said sample is a leucocyte fraction extract derived from human blood.

6. A method for simultaneously determining the presence of human MGMT and R-MGMT in a sample, which comprises:

(I) contacting the sample with V8 Protease or a functional modified form thereof;
   (II) separating the polypeptides of the treated sample by SDS-polyacrylamide gel electrophoresis; and
   (III) analysing the gel obtained in step (II) for the presence of (i) at least one polypeptide fragment characteristic of action of V8 Protease on R-MGMT and (ii) intact human MGMT.

7. A method as claimed in claim 6 wherein said analyzing step (III) is effected using a Western Analysis procedure.

8. A method as claimed in claim 7 wherein said Western Analysis is carried out using a monoclonal antibody reagent which recognises (i) intact SDS denatured human MGMT and (ii) both the 18 kD and 14 kD polypeptide fragments obtainable by V8 Protease cleavage of R-MGMT after separation by SDS-polyacrylamide gel electrophoresis.

9. A method as claimed in claim 8 wherein monoclonal antibody 2G1, obtainable from hybridoma cell line ECACC 93112516, or a functional equivalent thereof, is employed for said Western Analysis.

10. A method as claimed in claim 6 wherein said sample is a leucocyte fraction extract derived from human blood.

11. A kit for carrying out the method as claimed in claim 6 which comprises:
    (i) V8 Protease or a functional modified form thereof; and
    (ii) an antibody reagent which recognizes both intact human MGMT and a V8 Protease cleavage fragment of R-MGMT following separation by SDS-polyacrylamide gel electrophoresis.

12. The kit as claimed in claim 11 comprising:
    (i) V8 Protease or a functional modified form thereof; and
    (ii) monoclonal antibody 2G1, obtainable from hybridoma cell line ECACC 93112516, or a monoclonal antibody which competitively blocks binding of monoclonal antibody 2G1 to SDS denatured human MGMT.

13. A method of identifying an alkylating chemotherapeutic or carcinogenic agent in a sample which comprises:
    (i) contacting human cells in vitro with the said sample,
    (ii) preparing a cellular extract of cells thus treated, and,
    (iii) assaying R-MGMT in the cellular extract using an assay method as claimed in claim 1.

14. A method of assessing the potency of an alkylating chemotherapeutic or carcinogenic agent which comprises:
    (i) contacting populations of human cells in vitro with different concentrations of the said agent,
    (ii) preparing a cellular extract of cells from each population following treatment as in step (i), and
    (iii) assaying R-MGMT in each cellular extract using an assay method as claimed in claim 1.

15. Monoclonal antibody 2G1 obtainable from hybridoma cell line ECACC 93112516.

16. Hybridoma cell line ECACC 93112516.

* * * * *